(12) United States Patent
Anzai et al.

(10) Patent No.: US 12,404,485 B2
(45) Date of Patent: Sep. 2, 2025

(54) CELL CULTURE SUBSTRATE

(71) Applicant: TERUMO KABUSHIKI KAISHA, Tokyo (JP)

(72) Inventors: Takao Anzai, Kanagawa (JP); Ichiro Hirahara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 889 days.

(21) Appl. No.: 17/415,504

(22) PCT Filed: Dec. 18, 2019

(86) PCT No.: PCT/JP2019/049582
§ 371 (c)(1),
(2) Date: Jun. 17, 2021

(87) PCT Pub. No.: WO2020/130033
PCT Pub. Date: Jun. 25, 2020

(65) Prior Publication Data
US 2022/0049203 A1    Feb. 17, 2022

(30) Foreign Application Priority Data
Dec. 20, 2018   (JP) .................. 2018-238607

(51) Int. Cl.
*C12M 1/00* (2006.01)
*C12M 1/12* (2006.01)

(52) U.S. Cl.
CPC ............ *C12M 23/20* (2013.01); *C12M 25/14* (2013.01)

(58) Field of Classification Search
None
See application file for complete search history.

(56) References Cited

U.S. PATENT DOCUMENTS

| | | | |
|---|---|---|---|
| 3,726,943 A | 4/1973 | Joy | |
| 3,821,087 A | 6/1974 | Knazek et al. | |
| 5,037,656 A * | 8/1991 | Pitt .................... | B01D 67/0088 435/402 |
| 6,225,367 B1 | 5/2001 | Chaouk et al. | |
| 8,168,433 B2 | 5/2012 | Gehman et al. | |
| 8,354,274 B2 | 1/2013 | Fadeev et al. | |
| 2009/0191634 A1 | 7/2009 | Martin et al. | |
| 2012/0282697 A1 | 11/2012 | Henry et al. | |
| 2020/0056138 A1 | 2/2020 | Anzai et al. | |

FOREIGN PATENT DOCUMENTS

| | | |
|---|---|---|
| EP | 2598518 | 6/2013 |
| JP | H11-263819 | 9/1999 |
| JP | 2002-145971 | 5/2002 |
| JP | 2006-316169 | 11/2006 |
| JP | 2010-523118 | 7/2010 |
| JP | 2013-507143 | 3/2013 |
| JP | 2013-524854 | 6/2013 |
| JP | 2013-176377 | 9/2013 |
| JP | 2015-526093 | 9/2015 |
| JP | 2016-63801 | 4/2016 |
| JP | 2016-112397 | 6/2016 |
| JP | 2016-537001 | 12/2016 |
| JP | 2017-509344 | 4/2017 |
| JP | 2017-104028 | 6/2017 |
| JP | 2018-12811 | 1/2018 |
| WO | WO 2008/109674 | 9/2008 |
| WO | WO 2008/124229 | 10/2008 |
| WO | WO 2011/045644 | 4/2011 |
| WO | WO 2011/140231 | 11/2011 |
| WO | WO 2014/031666 | 2/2014 |
| WO | WO 2015/073918 | 5/2015 |
| WO | WO 2015/148704 | 10/2015 |
| WO | 2016159153 A1 | 6/2016 |
| WO | 2018008985 A2 | 11/2018 |

OTHER PUBLICATIONS

Mooney et al. Switching From Differentiation to Growth in Hepatocytes: Control by Extracellular Matrix. Journal of Cellular Physiology (1992), 151, 497-505. (Year: 1992).*
Hutcheon et al., "Water absorption and surface properties of novel poly(ethylmethacrylate) polymer systems for use in bone and cartilage repair," Biomaterials, vol. 22, 2001, pp. 667-676.
Lerman et al., "The Evolution of Polystyrene as a Cell Culture Material," Tissue Engineering: Part B, vol. 24, No. 5, 2018, pp. 359-372.
Patel et al., "A defined synthetic substrate for serum-free culture of human stem cell derived cardiomyocytes with improved functional maturity identified using combinatorial materials microarrays," Biomaterials, vol. 61, May 15, 2015, pp. 257-265.
Sato et al., "Blood-compatible poly(2-methoxyethyl acrylate) for the adhesion and proliferation of endothelial and smooth muscle cells," Colloids and Surfaces B: Biointerfaces, vol. 145, May 20, 2016, pp. 586-596.
Official Action (with English translation) for Japan Patent Application No. 2021-502910, dated May 23, 2023, 11 pages.
Official Action for U.S. Appl. No. 16/541,897, dated Sep. 13, 2021, 13 pages.

(Continued)

*Primary Examiner* — Sean C. Barron
(74) *Attorney, Agent, or Firm* — Sheridan Ross P.C.

(57) ABSTRACT

This invention is to provide a means capable of providing excellent cell proliferation activity to a hydrophilic polymer substrate. Provided is a cell culture substrate comprising a coating layer on at least one surface of a hydrophilic polymer substrate, wherein the coating layer includes a polymer comprising a structural unit derived from furfuryl (meth)acrylate represented by Formula, and a ratio of mass of the polymer contained per unit area of the coating layer is more than 2 µg/cm².

7 Claims, 1 Drawing Sheet

(56) References Cited

OTHER PUBLICATIONS

Official Action for U.S. Appl. No. 16/541,897, dated May 3, 2022, 15 pages.
Official Action for U.S. Appl. No. 16/541,897, dated Dec. 12, 2022, 19 pages.
Official Action for U.S. Appl. No. 16/541,897, dated May 22, 2023, 14 pages.
Notice of Allowance for U.S. Appl. No. 16/541,897, dated Aug. 28, 2023, 7 pages.
Official Action with Machine Translation for Japan Patent Application No. 2021-524053, dated Aug. 1, 2023, 7 pages.

* cited by examiner

CELL CULTURE SUBSTRATE

TECHNICAL FIELD

The present invention relates to a cell culture substrate excellent in cell proliferation activity and a bioreactor and a method for culturing a stem cell using the cell culture substrate.

BACKGROUND

In recent years, a cell culture technology has been used in the development of regenerative medicine or drug discovery. In particular, attention has been paid to use of stem cells, and technology for repairing and replacing damaged or defective tissues has been actively studied by using stem cells expanded from donor cells. Most of cells of animals including humans are adherent (scaffold-dependent) cells which cannot survive in a floating state and survive in a state of being adhered to something. For this reason, various developments of functional culture substrates for culturing adherent (scaffold-dependent) cells at high density to obtain cultured tissues similar to living tissues have been conducted.

As a cell culture substrate, plastic or glass vessels have been conventionally used, and it has been reported that a plasma treatment or the like is performed to a surfaces of these cell vessels. A substrate subjected to the treatment has excellent adhesion to cells, and can be used to grow cells and maintain their function.

Meanwhile, regarding a structure of the cell culture substrate (cell culture vessel), in addition to a conventional flat dish (plate) structure, various structures, such as a structure in which a porous body is inserted as a culture scaffold in a bag, a hollow fiber structure, a sponge structure, a flocculent (glass wool) structure, and a structure in which a plurality of dishes are laminated, have been developed. It is difficult or impossible to perform the plasma treatment to culture vessels having such various or complicated structures.

In this regard, as a method other than the plasma treatment, coating using a polymer compound promoting cell adhesion has been studied. For example, Non Patent Literature 1 discloses that cell adhesion to a cell culture substrate is improved by applying a solution containing a homopolymer of tetrahydrofurfuryl acrylate (PTHFA; polytetrahydrofurfuryl acrylate) to a surface of a cell culture substrate made of polystyrene.

CITATION LIST

Non Patent Literature

[NPL 1]
Non Patent Literature 1: Colloids and Surfaces B; Biointerfaces 145 (2016) 586-596.

SUMMARY OF THE INVENTION

The hollow fiber membrane used in the hollow fiber type bioreactor is typically subjected to a hydrophilization treatment for performing culture medium replacement. The present inventors have studied whether cell adhesion and cell proliferation activity are improved by applying the solution containing PTHFA described in Non Patent Literature 1 by a spin coating method to subject a hydrophilic polymer substrate to a surface treatment. As a result, it has been found that the cell proliferation activity is not sufficient and there is a need for further improvement. Therefore, regarding the cell culture substrate formed by a hydrophilic polymer compound like a hollow fiber membrane for a bioreactor, a further improvement in cell proliferation activity is required.

The present invention has been made in view of the above-described circumstances, and an object thereof is to provide a means capable of providing excellent cell proliferation activity to a hydrophilic polymer substrate.

The present inventors have conducted intensive studies to solve the above-described problems. As a result, the present inventors have found that the above-described problems can be solved by controlling the coating amount to be in a specific range when a surface of a hydrophilic polymer substrate is coated using a polymer comprising a structural unit (1) derived from furfuryl (meth)acrylate having a specific structure. The present invention has been completed on the basis of the above finding.

That is, the above object can be achieved by a cell culture substrate comprising a coating layer on at least one surface of a hydrophilic polymer substrate, wherein the coating layer contains a polymer comprising a structural unit (1) derived from furfuryl (meth)acrylate represented by the following Formula (1), and a ratio of mass of the polymer contained per unit area of the coating layer is more than 2 µg/cm².

[Chemical Formula 1]

Formula (1)

wherein, $R^1$ represents a hydrogen atom or a methyl group and $R^2$ represents a group represented by the following Formula (1-1) or the following Formula (1-2):

[Chemical Formula 2]

Formula (1-1)

Formula (1-2)

wherein, $R^3$ represents an alkylene group having 1 to 3 carbon atoms.

DETAILED DESCRIPTION

A cell culture substrate of the present invention is characterized by comprising a coating layer on at least one surface of a hydrophilic polymer substrate, wherein the coating layer contains a polymer comprising a structural unit (1) derived from furfuryl (meth)acrylate represented by the following Formula (1), and a ratio of mass of the polymer contained per unit area of the coating layer is more than 2 μg/cm²:

[Chemical Formula 3]

Formula (1)

wherein, $R^1$ represents a hydrogen atom or a methyl group and $R^2$ represents a group represented by the following Formula (1-1) or the following Formula (1-2):

[Chemical Formula 4]

Formula (1-1)

Formula (1-2)

wherein, $R^3$ represents an alkylene group having 1 to 3 carbon atoms.

According to the present invention, excellent cell proliferation activity can be provided to the hydrophilic polymer substrate.

In the present description, the furfuryl (meth)acrylate represented by the above Formula (1) is also simply referred to as "furfuryl (meth)acrylate" and the structural unit (1) derived from furfuryl (meth)acrylate represented by the above Formula (1) is also simply referred to as the "structural unit (1)". Further, the polymer comprising the structural unit (1) is also simply referred to as the "polymer" or the "polymer according to the present invention". Furthermore, the ratio of mass of the polymer contained per unit area of the coating layer is also simply referred to as the "coating amount of the polymer" or the "coating amount".

Further, in the present description, the term "(meth) acrylate" includes both acrylate and methacrylate". Similarly, the term "(meth)acrylic acid" includes both acrylic acid and methacrylic acid, and "(meth)acryloyl" includes both acryloyl and methacryloyl.

Further, in the present description, the term "hydrophilic" indicates that a contact angle of a surface of a target object to water is 50° or less, preferably 40° or less. Incidentally, in the present description, as the contact angle, a value measured by a contact angle meter (measurement method; according to JIS R 3257:1999 (sessile drop method)) is adopted.

The cell culture substrate of the present invention is characterized in that the coating layer containing the polymer is formed on at least one surface of the hydrophilic polymer substrate at a specific coating amount. The coating layer formed by using a specific coating amount of the polymer has excellent cell proliferation activity. Here, the mechanism for exhibiting the effects by the present invention is presumed to be as follows. Incidentally, the present invention is not limited to the following presumption.

As described above, in the cell culture technology using the hollow fiber type bioreactor, an improvement in cell adhesion to the hollow fiber membrane is required. The hollow fiber membrane used in the bioreactor is typically subjected to a hydrophilization treatment for performing culture medium replacement. However, the hollow fiber membrane subjected to the hydrophilization treatment has a problem in that cell adhesion is low. On the other hand, Non Patent Literature 1 discloses that cell adhesion to a cell culture substrate made of polystyrene is improved by subjecting the cell culture substrate to a surface treatment using polytetrahydrofurfuryl acrylate (PTHFA). In this regard, the present inventors have studied whether cell adhesion and cell proliferation activity are improved by applying the solution containing PTHFA described in Non Patent Literature 1 by a spin coating method to subject a hydrophilic polymer substrate to a surface treatment. As a result, it has been found that the cell proliferation activity is not sufficient and there is a need for further improvement (Comparative Example 1 described later).

In this regard, the present inventors have conducted intensive studies on a means for improving cell proliferation activity. As a result, the present inventors have found that by setting the coating amount of the polymer to be more than 2 μg/cm², cell proliferation activity is significantly improved.

When the hydrophilic polymer substrate is subjected to the surface treatment using the polymer, a coating layer having appropriate hydrophobicity (for example, having a surface with a contact angle to water of about 60 to 700) is formed on the hydrophilic polymer substrate. When cells are cultured using the hydrophilic polymer substrate comprising the coating layer, a cell adhesion factor (cell-adhesive protein) contained in the culture medium is favorably adsorbed to the coating layer, and it is presumed that the cells are easily attached therethrough. Further, it is considered that an integrin binding site of the cell-adhesive protein adsorbed to the surface faces the side of the cells to exhibit favorable cell proliferation activity.

Hereinafter, a preferred embodiment of the present invention will be described. Incidentally, the present invention is not limited only to the following embodiment.

In the present description, the term "X to Y" which indicates a range means the term "X or more and Y or less" including X and Y. Further, unless otherwise specified, operations and measurements of physical properties and the like are conducted under conditions of room temperature (20 to 25° C.)/relative humidity of 40 to 50% RH.

<Cell Culture Substrate>

The cell culture substrate of the present invention comprises a coating layer containing the polymer in a specific coating amount is formed on at least one surface of a hydrophilic polymer substrate.

When the coating layer containing the polymer in a specific coating amount according to the present invention is formed on the surface of the hydrophilic polymer substrate, excellent cell proliferation activity (cell extension ability) can be expressed. Further, the cell culture substrate comprising the coating layer containing the polymer according to the present invention is also excellent in cell adhesion. In addition, the coating layer containing the polymer according to the present invention can be simply formed in such a manner that the polymer is dissolved in a solvent and the resultant solution is applied to a surface of the hydrophilic polymer substrate. Therefore, by using the polymer according to the present invention, a coating layer having cell proliferation activity (and further cell adhesion) can be formed on surface of cell culture substrate (cell culture vessel) regardless of the shape or design.

(Coating Layer)

The coating layer contains a polymer described below in an amount of more than 2 μg/cm² per unit area. When a ratio of the amount of the polymer per unit area is 2 μg/cm² or less, there is a concern that sufficient cell proliferation activity is not obtainable. Further, the upper limit of the amount of the polymer per unit area is 100000 μg/cm² or less in consideration of other functions required in the cell culture substrate (such as culture medium permeability and gas exchangeability). Incidentally, the ratio is preferably 10 μg/cm² or more and 700 μg/cm² or less, more preferably 36 μg/cm² or more and 600 μg/cm² or less, further preferably 60 μg/cm² or more and 500 μg/cm² or less, and particularly preferably 100 μg/cm² or more and 400 μg/cm² or less. With the above ratio, both cell adhesion activity and cell proliferation activity can be achieved with balance.

Incidentally, the mass per unit area of the polymer can be obtained as a value obtained by dividing a difference between masses of the membrane before and after coating of the coating layer by the surface area, as described in Examples described later, in a case where the coating layer is formed by only the polymer. Further, in a case where the difference between masses of the membrane before and after coating is unclear or a case where the coating layer contains other components other than the polymer, the mass per unit area of the polymer can be measured by an analysis method using GPC as described below. That is, the cell culture substrate on which the coating layer is formed is cut into 3 g, this cut substrate is filled in a glass tube equipped with a screw cap, 25 ml of acetone is added thereto, and the resultant mixture is stirred for 120 minutes, so that all of the polymers contained in the coating layer are extracted. The whole amount of the acetone extract is transferred to another glass tube equipped with a screw cap and acetone is vaporized using a heat block. To the glass tube in which the vaporized dry product is present, 10 ml of tetrahydrofuran to dissolve the vaporized dry product. Meanwhile, THF solutions containing the respective polymers according to the present invention at a ratio of 1000 μg/ml (standard solutions) are prepared respectively, these solutions are analyzed using GPC, and then areas of peaks corresponding to the respective polymers are calculated. Subsequently, the vaporized dry product THF solutions (test solutions) are analyzed using GPC, and then, similarly, areas of peaks corresponding to the respective polymers are calculated. Thereafter, regarding each polymer, the amount of the polymer in the test solution is calculated using the following Equation 1 and the ratio of mass of the polymer per unit area of the coating layer is calculated using the following Equation 2. The sum of the ratios of the respective polymers obtained by Equation 2 corresponds to the ratio of mass of the polymer contained per unit area of the coating layer.

[Math. 1]

Amount (μg) of polymer in test solution=(Peak area of test solution÷Peak area of standard solution)×10    (Equation 1)

Ratio of mass (μg/cm²) of polymer contained per unit area of coating layer=Amount (μg) of polymer in test solution÷Mass (g) of cell culture substrate provided to extraction×Membrane area (cm²) per 1 g of cell culture substrate    (Equation 2)

(Polymer)

The polymer according to the present invention has a structural unit (1) derived from furfuryl (meth)acrylate represented by the following Formula (1). By using the polymer, excellent cell proliferation activity (and further cell adhesion) can be provided to the hydrophilic polymer substrate. In addition, by applying a solution of the polymer to a surface of a hydrophilic polymer substrate, a coating layer can be simply formed on a substrate having various shapes. Therefore, by using the polymer according to the present invention, a coating layer having excellent in cell proliferation activity (and further cell adhesion) can be formed on a cell culture substrate (cell culture vessels) having various shapes or designs.

The polymer according to the present invention essentially includes the structural unit (1), but may further have a structural unit derived from other monomer in addition to the structural unit (1). Here, another monomer is not particularly limited as long as it does not inhibit cell adhesion. Specific examples of the another monomer include acrylamide, N,N-dimethylacrylamide, N,N-diethylacrylamide, methacrylamide, N,N-dimethylmethacrylamide, N,N-diethylmethacrylamide, ethylene, propylene, N-vinylacetamide, N-isopropenyl acetamide, N-(meth)acryloyl morpholine, and the like. These other monomers may be used singly or in combination of two or more kinds thereof. A composition of the structural unit derived from another monomer in a case where the polymer further has a structural unit derived from another monomer is not particularly limited as long as it does not inhibit cell adhesion, but the composition of the structural unit derived from another monomer is preferably more than 0% by mole and less than 10% by mole and more preferably about 3 to 8% by mole with respect to the structural unit (1).

However, from the viewpoint of further improving cell proliferation activity (and further cell adhesion), it is preferable that the polymer includes no structural units derived from another monomer, that is, is composed of by only the structural unit (1). That is, according to a preferred embodiment of the present invention, the polymer is composed of the structural unit (1).

(Structural Unit (1))

The structural unit (1) is derived from furfuryl (meth) acrylate of the following Formula (1). Incidentally, the structural unit (1) constituting the polymer may be used singly or in combination of two or more kinds thereof. That is, the structural unit (1) may be composed of only one kind of the structural unit derived from furfuryl (meth)acrylate of the following Formula (1) or may be composed of two or more kinds of the structural units derived from furfuryl (meth)acrylate of the following Formula (1). In the latter case, each structural unit may be present in the form of block or random.

[Chemical Formula 5]

Formula (1)

[Chemical Formula 6]

Formula (1-1)

-continued

Formula (1-2)

In the Formula (1), $R^1$ is a hydrogen atom or a methyl group.

$R^2$ represents a group represented by the above Formula (1-1) or Formula (1-2). Among these, from the viewpoint of, further improving cell proliferation activity (and further cell adhesion), or the like, $R^2$ preferably represents a group represented by the Formula (1-1). In the Formulae (1-1) and (1-2), $R^3$ represents an alkylene group having 1 to 3 carbon atoms. Herein, as the alkylene group having 1 to 3 carbon atoms, there are a methylene group (—$CH_2$—), an ethylene group (—$CH_2CH_2$—), a trimethylene group (—$CH_2CH_2CH_2$—), and a propylene group (—$CH(CH_3)CH_2$— or —$CH_2CH(CH_3)$—). Of them, from the viewpoint of further improvement in cell proliferation activity (and further cell adhesion), $R^3$ preferably represents a methylene group (—$CH_2$—) or an ethylene group (—$CH_2CH_2$—), and more preferably represents a methylene group (—$CH_2$—).

That is, as the furfuryl (meth)acrylate, there are tetrahydrofurfuryl acrylate, tetrahydrofurfuryl methacrylate, furfuryl acrylate, furfuryl methacrylate, 5-[2-(acryloyloxy)ethyl]tetrahydrofuran, 5-[2-(methacryloyloxy)ethyl]tetrahydrofuran, 5-[2-(acryloyloxy)ethyl]furane, 5-[2-(methacryloyloxy)ethyl]furane, and the like. These may be used singly or in combination of two or more kinds thereof. Of them, from the viewpoint of further improvement in cell proliferation activity (and further cell adhesion), tetrahydrofurfuryl (meth)acrylate is preferred and tetrahydrofurfuryl acrylate (THFA) is more preferred.

A weight average molecular weight (Mw) of the polymer is not particularly limited, and is preferably 50,000 to 800,000. Within the above range, the solubility of the polymer in a solvent can be improved and application to a substrate is uniformly conducted with ease. From the viewpoint of improving coating film formability, the weight average molecular weight of the polymer is more preferably 100,000 to 500,000, and particularly preferably 150,000 to 350,000.

In the present description, as the "weight average molecular weight (Mw)," a value measured by gel permeation chromatography (GPC) using polystyrene as a standard substance and tetrahydrofuran (THF) as a mobile phase respectively is adopted. Specifically, the polymer is dissolved in tetrahydrofuran (THF) so as to have a concentration of 10 mg/ml, thereby preparing a sample. Regarding the sample prepared as above, GPC column LF-804 (manufactured by Showa Denko K.K.) is attached to a GPC system LC-20 (manufactured by SHIMADZU CORPORATION), THF is supplied as a mobile phase, and polystyrene is used as a standard substance, to measure GPC of the polymer. After preparing a calibration curve with a standard polystyrene, the weight average molecular weight (Mw) of the polymer is calculated on the basis of this curve.

The polymer according to the present invention is not particularly limited, and for example, can be produced by employing a conventionally known polymerization method such as bulk polymerization, suspension polymerization, emulsion polymerization, solution polymerization, a living radical polymerization method, a polymerization method using a macroinitiator, a polycondensation method, or the like.

In the method, a polymerization solvent which can be used in the preparation of the monomer solution is not particularly limited as long as it can dissolve the monomer used above. Examples thereof include aqueous solvents such as water, alcohol such as methanol, ethanol, propanol, or isopropanol, and polyethylene glycols; aromatic solvents such as toluene, xylene, and tetralin; halogen-based solvents such as chloroform, dichloroethane, chlorobenzene, dichlorobenzene, and trichlorobenzene; and the like. Among these, taking in consideration of easy dissolution of the monomer, or the like, methanol or ethanol is preferable. Further, a concentration of the monomer in the monomer solution is not particularly limited, but the concentration of the monomer in the monomer solution is typically 15 to 60% by mass, more preferably 20 to 50% by mass, and particularly preferably 25 to 45% by mass. Incidentally, the concentration of the monomer means a total concentration of the furfuryl (meth)acrylate of the Formula (1) and if being used, a monomer which is copolymerizable with this component (another monomer, copolymerizable monomer).

A polymerization initiator is not particularly limited, and a known polymerization initiator may be used. From the viewpoint of high polymerization stability, the polymerization initiator is preferably a radical polymerization initiator. Specific examples thereof include persulfates such as potassium persulfate (KPS), sodium persulfate, and ammonium persulfate; peroxides such as hydrogen peroxide, t-butyl peroxide, and methyl ethyl ketone peroxide; and azo compounds such as azobisisobutyronitrile (AIBN), 2,2'-azobis(4-methoxy-2,4-dimethylvaleronitrile), 2,2'-azobis(2, 4-dimethylvaleronitrile), 2,2'-azobis[2-(2-imidazoline-2-yl)propane]dihydrochloride, 2,2'-azobis[2-(2-imidazoline-2-yl)propane]disulfate dihydrate, 2,2'-azobis(2-methylpropionamidine)dihydrochloride, 2,2'-azobis[N-(2-carboxyethyl)-2-methylpropionamidine)]hydrate, 3-hydroxy-1, 1-dimethylbutyl peroxyneodecanoate, α-cumylperoxy neodecanoate, 1, 1, 3, 3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl)peroxydicarbonate, di(secondary butyl)peroxydicarbonate, and azobiscyanovaleric acid. Further, for example, a reducing agent such as sodium sulfite, sodium hydrogen sulfite, or ascorbic acid may be used in combination with the radical polymerization initiator as a redox type initiator. A blending amount of the polymerization initiator is preferably 0.5 to 5 mmol with respect to 1 mol of a total amount of the monomers. With such a blending amount of the polymerization initiator, polymerization of the monomers is efficiently proceed.

The polymerization initiator as it is may be mixed with the furfuryl (meth)acrylate of the Formula (1), if being used, a monomer which is copolymerizable with this component (another monomer, copolymerizable monomer), and a polymerization solvent, or alternatively a solution of the polymerization initiator obtained by being dissolved in another solvent in advance may be mixed with the monomers and the polymerization solvent. In the latter case, another solvent used to dissolve the polymerization initiator is not particularly limited as long as it can dissolve the polymerization initiator, but the same solvent as the polymerization solvent described above can be exemplified. Further, another solvent may be the same as or different from the polymerization solvent, but in consideration of easy control of polymerization, and the like, the same solvent as the polymerization solvent is preferably used. Further, in this case, a concentration of the polymerization initiator in another solvent is not particularly limited, but in consideration of easy mixing, and the like, the addition amount of the polymerization initiator is preferably 0.1 to 10 parts by mass and more preferably 0.5 to 5 parts by mass with respect to 100 parts by mass of another solvent.

Further, in the case of using the polymerization initiator in the solution state, a deaeration treatment may be performed in advance before adding a solution in which the monomers (furfuryl (meth)acrylate, and a copolymerizable monomer which is used as optionally) are dissolved in the polymerization solvent, to the polymerization initiator solution. For the deaeration treatment, for example, an inert gas such as nitrogen gas or argon gas may be blown for about 10 seconds to 5 hours into the above-described solution. In the deaeration treatment, the solution may be adjusted to about 30° C. to 80° C., preferably to a polymerization temperature in a polymerization step as described below.

Next, the monomer solution is heated to polymerize the monomers. Here, as the polymerization method, for example, a known polymerization method such as radical polymerization, anionic polymerization, or cationic polymerization can be adopted, and radical polymerization which facilitates production is preferably used.

Polymerization conditions are not particularly limited as long as the furfuryl (meth)acrylate of the Formula (1), and if being used, a monomer which is copolymerizable with this component (another monomer, copolymerizable monomer) can be polymerized. Specifically, the polymerization temperature is preferably 30° C. to 80° C. and more preferably 40° C. to 55° C. Further, the polymerization time is preferably is 1 to 24 hours and more preferably 5 to 12 hours. Under such conditions, polymerization of the monomers can efficiently proceed. Further, it is possible to effectively suppress or prevent gelation in the polymerization step and to achieve high production efficiency.

As necessary, a chain transfer agent, a polymerization rate-adjusting agent, a surfactant, and other additives may be appropriately used during the polymerization.

An atmosphere under which the polymerization reaction is carried out is not particularly limited, and the reaction can be carried out under an air atmosphere, an inert gas atmosphere such as nitrogen gas or argon gas, and the like. Further, during the polymerization reaction, the reaction solution may be stirred.

The polymer after polymerization can be purified by a general purification method such as a reprecipitation method (precipitation method), a dialysis method, an ultrafiltration method, or an extraction method.

The purified polymer can be dried by an arbitrary method such as freeze drying, vacuum drying, spray drying, or heat drying, but freeze drying or vacuum drying is preferred from the viewpoint that the physical properties of the polymer are less affected.

(Hydrophilic Polymer Substrate)

In the present invention, a coating layer containing the polymer is formed on at least one surface of the hydrophilic polymer substrate. Here, the hydrophilic polymer substrate refers to a polymer substrate, of which a surface being hydrophilic (that is, a contact angle of the surface of the polymer substrate to water being 50° or less, preferably 40° or less). Incidentally, the lower limit of the contact angle of the hydrophilic polymer substrate to water is not particularly limited (lower limit is 0). The contact angle of the surface of the polymer substrate to water, in a case where a substrate before a coating layer is formed is available, can be obtained by measuring the substrate before a coating layer is formed with a contact angle meter (measurement method; according to JIS R 3257:1999 (sessile drop method)). Meanwhile, the contact angle of a polymer substrate obtained by cleansing a cell culture substrate with an organic solvent or the like such as alcohol to remove the coating layer can also be obtained by the measurement method described above.

The coating layer is formed on at least a surface with which cells of the hydrophilic polymer substrate contact (for example, on which a liquid containing cells flows or cells are cultured). Further, it is not necessary that the coating layer is formed on the entire surface of the hydrophilic polymer substrate. The coating layer may be formed on a portion (a part) of the surface of the hydrophilic polymer substrate with which cells contact (for example, on which a liquid containing cells flows or cells are cultured). From the viewpoint of further improving cell proliferation activity (and further cell adhesion), the coating layer is preferably formed on the entire surface of the hydrophilic polymer substrate at the side with which cells contact (for example, on which a liquid containing cells flows or cells are cultured).

A material constituting the hydrophilic polymer substrate is not particularly limited, and examples thereof include hydrophobic polymers such as polyamide (PA), polyaramide (PAA), polyethersulfone (PES), polyarylethersulfone (PAES), polysulfone (PSU), polyarylsulphone (PASU), polycarbonate (PC), polyether, polyurethane (PUR), polyetherimide, polypropylene, polyethylene, polystyrene, polyacrylonitrile, and polytetrafluoroethylene; hydrophilic polymers such as polyvinylpyrrolidone (PVP), polyethylene glycol (PEG), polyglycolmonoester, water soluble cellulosic derivatives, polysorbate, and polyethylene-polypropylene oxide copolymers; and the like. The hydrophobic polymer may be used singly or as a mixture of two or more kinds thereof. The hydrophilic polymer may be used singly or as a mixture of two or more kinds thereof.

In an embodiment of the present invention, the hydrophilic polymer substrate preferably contains at least one selected from the group consisting of polyamide (PA), polyethersulfone (PES), polyarylethersulfone (PAES), and polyvinylpyrrolidone (PVP). The hydrophilic polymer substrate containing such a material is suitably used as a hollow fiber membrane of a bioreactor.

The hydrophilic polymer substrate according to the present invention may be composed of a mixture of the hydrophobic polymer and the hydrophilic polymer or may contain, for example, a mixture of polyamide (PA), polyarylethersulfone (PAES), and polyvinylpyrrolidone (PVP). The hydrophilic polymer substrate containing such a material is particularly suitably used as a hollow fiber membrane of a bioreactor. In a case where the hydrophilic polymer substrate contains a mixture of the hydrophobic polymer and the hydrophilic polymer, for example, a content of the hydrophobic polymer may be 65 to 95% by mass and the content of the hydrophilic polymer may be 5 to 35% by mass with respect to a total amount of the hydrophobic polymer and the hydrophilic polymer.

A structure of the hydrophilic polymer substrate is not limited, and in addition to the plane structure, the hydrophilic polymer substrate can be designed in various structures (forms) such as a structure in which a porous body is inserted, a hollow fiber structure, a porous membrane structure, a sponge structure, and a flocculent (glass wool) structure. As described later, the cell culture substrate of the present invention can be suitably used in a bioreactor, particularly, a hollow fiber type bioreactor. Therefore, the hydrophilic polymer substrate preferably has hollow fibers and is more preferably a porous membrane (hollow fiber membrane) formed of a plurality of hollow fibers.

An inner diameter (diameter) of the hollow fibers is not particularly limited, but is preferably 50 to 1,000 μm, more preferably 100 to 500 μm, and particularly preferably about 150 to 350 μm. Further, an outer diameter (diameter) of the hollow fibers is not particularly limited, but is preferably 100 to 1,200 μm, more preferably 150 to 700 μm, and particularly preferably about 200 to 500 μm. A length of the hollow fibers is not particularly limited, but is preferably 50 to 900 mm, more preferably 100 to 700 mm, and particularly preferably about 150 to 500 mm. The number of the hollow fibers constituting the hollow fiber membrane is not particularly limited, but is, for example, about 1,000 to 100,000, more preferably 3,000 to 50,000, and particularly preferably about 5,000 to 25,000. In an embodiment, the hydrophilic polymer substrate is configured by about 9,000 hollow fibers having an average length of about 295 mm, an average inner diameter of 215 μm, and an average outer diameter of 315 μm. Herein, the coating layer may be formed on the inner side or the outer side of the hollow fiber membrane, but is preferably formed on the inner (lumen) surface.

An outer layer of the hollow fiber may have an open pore structure with a certain surface roughness. An opening (diameter) of the pore is not particularly limited, but is in the range of about 0.5 to about 3 μm, and the number of pores on the outer surface of the hollow fiber may be in the range of about 10,000 to about 150,000 per 1 square millimeter (1 mm$^2$). A thickness of the outer layer of the hollow fiber is not particularly limited, and for example, is in the range of about 1 to about 10 μm. The hollow fiber may have an additional layer (second layer) on the outer side, and at this time, the additional layer (second layer) preferably has a sponge structure having a thickness of about 1 to about 15 μm. The second layer having such a structure can serve as a support for the outer layer. Further, in this embodiment, the hollow fiber may have a further additional layer (third layer) at the outer side of the second layer. In this embodiment, the further additional layer (third layer) preferably has a finger-like structure. With the third layer having such a structure, mechanical stability is obtainable. Further, a high void volume with low resistance to membrane transfer of molecules can be provided. In this embodiment, during use, the finger-like voids are filled with a fluid and the fluid lowers resistance for diffusion and convection as compared with a matrix with a sponge-filled structure having a lower void volume. This third layer has a thickness of, preferably, about 20 to about 60 μm.

A method for producing a hollow fiber and a porous membrane is not particularly limited, and a known production method can be applied similarly or appropriately modified. For example, it is preferable that micro fine holes are formed on a wall of hollow fiber by a stretching method or a solid-liquid phase separation method.

The hollow fiber membrane used in a bioreactor is typically subjected to a hydrophilization treatment for performing culture medium replacement inside and outside the hollow fiber membrane. However, in a case where cells are cultured using such a hydrophilic polymer substrate, since a cell adhesion factor (cell-adhesive protein) contained in the culture medium is hardly adsorbed to the substrate, cell adhesion is poor. In this regard, when the surface treatment of the hydrophilic polymer substrate is performed using the polymer, the surface of the substrate is excessively hydrophobized (for example, the contact angle to water becomes about 60 to 70°), so that the cell adhesion factor is easily adsorbed.

A method for producing the hydrophilic polymer substrate is not particularly limited, and examples thereof include (i) a method in which a hydrophilic polymer substrate is produced using the hydrophilic polymer or using a mixture of the hydrophobic polymer and the hydrophilic polymer by a conventionally known method, (ii) a method in which a polymer substrate is produced using the hydrophobic polymer or using a mixture of the hydrophobic polymer and the hydrophilic polymer by a conventionally known method and then a surface of the polymer substrate is hydrophilized using a known means such as a plasma treatment, a corona treatment, or a primer treatment, and the like.

As the hydrophilic polymer substrate, commercially available products may be used, and examples thereof include Polyflux (registered trademark) manufactured by Baxter Limited, Desmopan (registered trademark) manufactured by DIC Covestro Polymer Ltd., and the like.

(Method of Forming Coating Layer) A method of forming a coating layer containing the polymer according to the present invention on the surface of the hydrophilic polymer substrate is not particularly limited. For example, in a case where the surface of the hydrophilic polymer substrate has a flat dish (plate) structure, a method of applying a polymer-containing solution obtained by dissolving the polymer according to the present invention to a predetermined surface (for example, adding to a well) and then drying the polymer-containing solution can be used. Further, for example, in a case where the hydrophilic polymer substrate is hollow fibers or a porous membrane, a method of bringing a polymer-containing solution obtained by dissolving the polymer according to the present invention into contact with a cell contact portion of the hollow fiber (for example, by flowing on an inner surface (lumen) or an outer surface of the hollow fiber) and then drying the polymer-containing solution can be used. Incidentally, in a case where the hydrophilic polymer substrate is a porous membrane formed by a plurality of hollow fibers, coating with a polymer-containing solution may be performed with respect to one hollow fiber and then the hollow fibers may be bundled or a plurality of hollow fibers are bundled to produce a porous membrane and then the coating may be performed.

Herein, a solvent for dissolving the polymer according to the present invention, a solvent having a small influence (deformation, cracks, breakage, or the like) to the cell culture substrate is suitable. Examples of such a solvent include aqueous solvents such as water, alcohol such as methanol, ethanol, propanol, or isopropanol, and polyethylene glycols; ketone-based solvents such as acetone; furan-based solvents such as tetrahydrofuran; and the like. The solvent may be used singly or in the form of a mixture of two or more kinds thereof. Among these, in consideration of further improvement in solubility of the polymer according to the present invention, and the like, the solvent is preferably a mixed solvent of water and alcohol. The alcohol used in the mixed solvent is preferably lower alcohol having 1 to 4 carbon atoms from the viewpoint of improving solubility of the polymer, particularly, methanol, ethanol, propanol, or isopropanol is preferred, and isopropanol is particularly preferred. That is, the solvent is preferably composed of water and isopropanol. Herein, a mixing ratio of water and isopropanol is not particularly limited, and for example, the mixing ratio (volume ratio) of water:isopropanol is preferably 1:1 to 50 and more preferably 1:5 to 15. Further, a concentration of the polymer in the polymer-containing solution is not particularly limited. In consideration of easy application to the substrate, the effect of reducing coating unevenness, and the like, the concentration thereof is preferably 0.0001 to 5% by mass and more preferably 0.001 to 2% by mass.

Further, a method of coating the polymer is not particularly limited, and a conventionally known method such as filling, dip coating (immersion method), spraying, spin coating, dropping, doctor blade, brush coating, roll coater, air knife coating, curtain coating, wire bar coating, gravure coating, or mixed solution-impregnated sponge coating can be applied.

Further, conditions for forming the coating film of the polymer are not particularly limited. For example, a contact time of the polymer-containing solution and the hydrophilic polymer substrate (for example, a time for circulating the polymer-containing solution to a lumen or an outer surface of the hollow fiber) is preferably 1 to 5 minutes and more preferably 1 to 3 minutes in consideration of easy formation of the coating film (thus coating layer), the effect of reducing coating unevenness, and the like. Further, a contact temperature of the polymer-containing solution and the hydrophilic polymer substrate (for example, a temperature at which the polymer-containing solution is circulated to a lumen or an outer surface of hollow fiber) is preferably 5 to 40° C. and more preferably 15 to 30° C. in consideration of easy formation of the coating film (thus coating layer), the effect of reducing coating unevenness, and the like.

An amount of the polymer-containing solution applied to a surface of the hydrophilic polymer substrate is not particularly limited, but is preferably such an amount that a ratio of mass per unit area of the polymer in the coating layer after drying is in the above range. Incidentally, in a case where such an amount cannot be obtainable by single contact (application), an application step (or the application step and a drying step described later) may be repeated until a desired applied amount is obtainable.

Next, by drying the coating film after the contact of the hydrophilic polymer substrate and the polymer-containing solution, the coating layer (coating film) by the polymer according to the present invention is formed on the surface of the hydrophilic polymer substrate. Herein, drying conditions are not particularly limited as long as the coating layer (coating film) by the polymer according to the present invention can be formed. Specifically, a drying temperature is preferably 5 to 50° C. and more preferably 15 to 40° C. A drying step may be performed under a single condition or may be performed stepwise under different conditions. Further, a drying time is not particularly limited, but is, for example, about 1 to 60 hours. Further, in a case where the hydrophilic polymer substrate is a porous membrane (hollow fiber membrane), the coating film may be dried by allowing a gas of 5 to 40° C. and more preferably 15 to 30° C. to continuously or gradually circulate on a surface of hollow fiber to which the polymer-containing solution is applied. Herein, the gas is not particularly limited as long as it has no influence on the coating film (coating layer) and can dry the coating film. Specific examples thereof include air, an inert gas such as nitrogen gas or argon gas, and the like. Further, a circulation amount of the gas is not particularly limited as long as the coating film can be sufficiently dried. The circulation amount of the gas is preferably 5 to 150 L/min and more preferably 30 to 100 L/min.

According to such a method, a coating layer containing the polymer according to the present invention can be efficiently formed on the hydrophilic polymer substrate. Incidentally, depending on the type of cells to be adhered, the hydrophilic polymer substrate may be further treated by a cell adhesion factor such as fibronectin, laminin, or collagen. With such a treatment, adhesion of cells to the substrate surface and growth of cells can be further promoted. Incidentally, in a case where the hydrophilic polymer substrate is a porous membrane formed of a plurality of hollow fibers, the treatment with a cell adhesion factor may be performed with respect to one hollow fiber and then the hollow fibers may be bundled or a plurality of hollow fibers are bundled to produce a porous membrane and then the treatment may be performed. Further, the treatment with a cell adhesion factor may be performed after the coating layer containing the polymer according to the present invention is formed, before the coating layer containing the polymer according to the present invention is formed, or at the same time the coating layer containing the polymer according to the present invention is formed.

In the present invention, a thickness (dry thickness) of the coating layer formed on the hydrophilic polymer substrate is preferably 0.005 to 20 μm.

<Bioreactor>

The cell culture substrate of the present invention shows excellent in cell proliferation activity (and further cell adhesion). Therefore, the cell culture substrate of the present invention can be suitably used in a bioreactor. That is, the present invention provides a bioreactor including the cell culture substrate of the present invention. Here, the bioreactor may be a plane type bioreactor or a hollow fiber type bioreactor, but is particularly preferably a hollow fiber type bioreactor. Therefore, in the following description, although a hollow fiber type bioreactor will be described as a preferred embodiment, the bioreactor of the present invention may be a plane type bioreactor, and in this case, the following embodiment can be appropriately changed and applied. Further, dimensional ratios in the drawings are exaggerated for the sake of explanatory convenience and may differ from actual ratios.

The bioreactor in which the cell culture substrate of the present invention can be suitably used is not particularly limited, but the cell culture substrate and the bioreactor of the present invention can be applied, for example, to cell culture/expansion systems described in JP 2010-523118 A (JP 5524824 B2)(WO 2008/124229 A2), JP 2013-524854 A (JP 6039547 B2) (WO 2011/140231 A1), JP 2013-507143 A (JP 5819835 B2) (WO 2011/045644 A1), JP 2013-176377 A (WO 2008/109674), JP 2015-526093 A (WO 2014/031666 A1), JP 2016-537001 A (WO 2015/073918 A1), JP 2017-509344 A (WO 2015/148704 A1), and the like; and Quantum Cell Expansion System manufactured by TERUMO BCT, INC. Conventionally, in the cell culture, facilities such as an incubator, a safety cabinet, and a clean room are separately needed, but the culture system as described above has all of those functions so that the facilities can be very simplified. Further, by controlling temperature or gas during the cell culture using the system as described above, a functionally closed system can be ensured and the cell culture can be performed automatically and in a closed environment.

Hereinafter, an embodiment of the bioreactor of the present invention will be described with reference to the drawings, but the present invention is not limited to the following embodiment.

Figure 1:
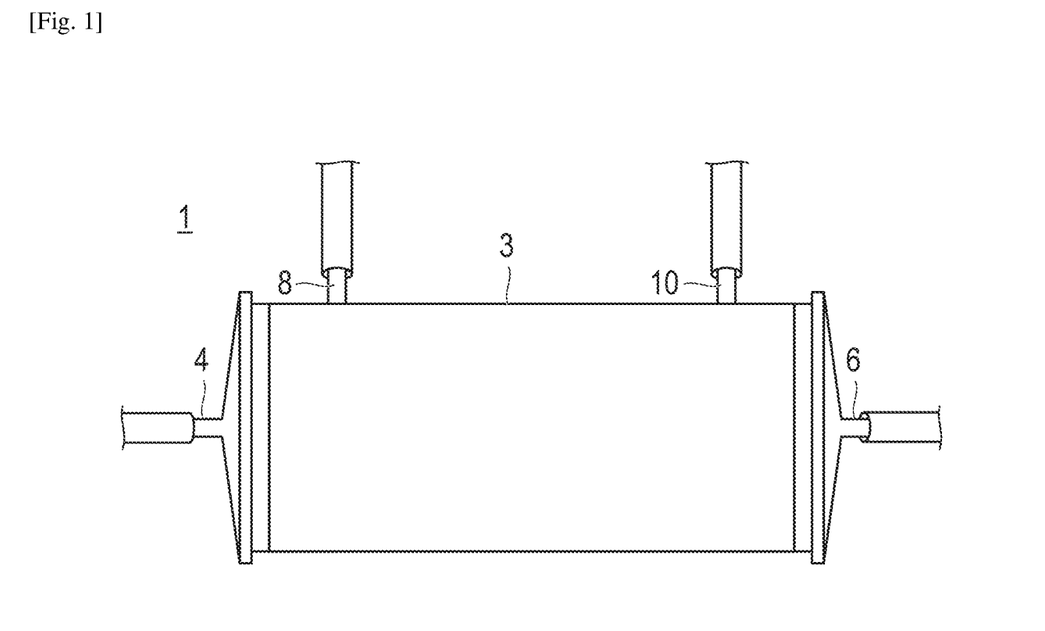
FIG. 1 is a partial side view illustrating an embodiment of a bioreactor (hollow fiber type bioreactor) of the present invention.
Figure 2:
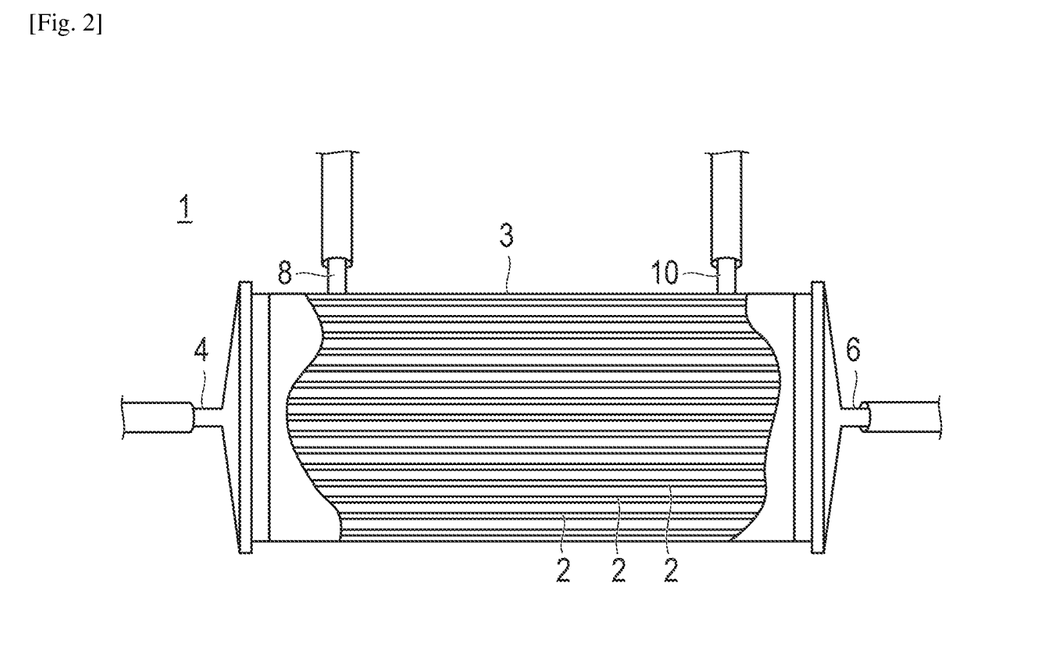
FIG. 2 is a partially cut-away side view of the bioreactor of FIG. 1.

FIG. 1 is a partial side view illustrating an embodiment of a bioreactor (hollow fiber type bioreactor) of the present invention. Further, FIG. 2 is a partially cut-away side view of the bioreactor of FIG. 1. In FIGS. 1 and 2, a bioreactor 1 has a cell culture substrate 2 of the present invention provided in a cell culture chamber 3. The cell culture chamber 3 has four openings, that is, four ports (an inlet port 4, an outlet port 6, an inlet port 8, and an outlet port 10). Herein, a culture medium including cells flows to a hollow fiber intracapillary (IC) space of the cell culture substrate 2 in the cell culture chamber 3 through the inlet port 4, and discharged from the outlet port 6. According to this, cells are efficiently adhered (attached) to and cultured on the surface of the hollow fiber lumen. Meanwhile, a culture medium or gas (such as oxygen or carbon dioxide) flows to be in contact with a hollow fiber extracapillary (EC) space of the cell culture substrate 2 in the cell culture chamber 3 through the inlet port 8, and discharged from the outlet port 10. According to this, in the cell culture chamber 3, small molecules such as culture medium components flow into the hollow fibers or unnecessary components are discharged from the inside of the hollow fibers, and cells adhered onto the surface of the hollow fibers are cultured. Further, after culturing for a predetermined time, a liquid (for example, PBS) containing trypsin is introduced into the intracapillary (IC) space of the hollow fiber of the cell culture substrate 2 in the cell culture chamber 3 through the inlet port 4, and then is held for a predetermined time (for example, about 5 to 10 minutes). Next, a culture medium or an isotonic solution such as PBS flows in the intracapillary (IC) space of the hollow fiber of the cell culture substrate 2 in the cell culture chamber 3 through the inlet port 4 to apply a shear force to cells, the cells are released from the inner wall of the hollow fiber, and the cells are recovered from the bioreactor through the outlet port 6. Incidentally, although the cells are adhered to the intracapillary (IC) space of the hollow fiber in the above embodiment, the present invention is not limited to the above embodiment, and cells may be cultured in such a manner that a culture medium containing cells flows into the outlet port 10 from the inlet port 8, the cells are efficiently adhered (attached) to an outer surface of the hollow fiber, and the culture medium flows into the outlet port 6 from the inlet port 4 in an hollow fiber lumen. Further, the fluid from the inlet port 4 into the outlet port 6 may flow in either a co-current or counter-current direction with respect to flow of fluid into the outlet port 10 from the inlet port 8.

(Use of Bioreactor)

As mentioned above, the bioreactor of the present invention includes a cell culture substrate excellent in cell proliferation activity (and further cell adhesion). Herein, cells which can be cultured in the bioreactor of the present invention may be adherent (scaffold-dependent) cells, non-adherent cells, or any combination thereof, but since the bioreactor is provided with the cell culture substrate excellent in cell adhesion, the bioreactor of the present invention can be particularly suitably used in culturing of adherent (scaffold-dependent) cells. Herein, as the adherent (scaffold-dependent) cells, there are animal cells such as stem cells including mesenchymal stem cell (MSC) or the like, fibroblast cells, and the like. As mentioned above, attention has been paid to stem cells in development of regenerative medicine or drug discovery. Therefore, the bioreactor of the present invention can be suitably used in culturing of stem cells. That is, the present invention provides a method for culturing a stem cell using the bioreactor of the present invention. Herein, the method for culturing a stem cell is not particularly limited, and a general culturing method can be applied similarly or appropriately modified.

EXAMPLES

The effects of the present invention will be described using the following examples and comparative examples. However, the technical scope of the present invention is not limited to only the following examples. Incidentally, in the following examples, operations were carried out at room temperature (25° C.) unless otherwise specified. In addition, unless otherwise specified, "%" and "part(s)" mean "% by mass" and "part(s) by mass," respectively.

Production of Polymer

Production Example 1: Synthesis of Polymer 1

To a 20-ml glass pressure-proof test tube, 2.00 g (0.0128 mol) of tetrahydrofurfuryl acrylate and 3 g of methanol were added, and then nitrogen gas was bubbled for 10 seconds. Then, 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours. The polymerization liquid was added to 50 ml of hexane, and the precipitated polymer component was recovered and dried under reduced pressure, thereby obtaining polytetrahydrofurfuryl acrylate (PTHFA) (polymer 1). The weight average molecular weight of the polymer 1 was 470000.

Coating to Hydrophilic Polymer Substrate

Example 1

The polymer 1 obtained in Production Example 1 described above was dissolved in a mixed solvent of water: isopropanol at a mixing ratio (volume ratio) of 1:9 to prepare a polymer solution having a concentration of 1.0% by mass. A commercially available hydrophilic polyether sulfone membrane (hydrophilic PES membrane, pore size: 0.1 μm, surface area: 20 $cm^2$, manufactured by Membrane Solutions Limited, contact angle of the surface to water: 20°) was immersed in the polymer solution and left to stand still at 25° C. for 2 minutes. The hydrophilic PES membrane was taken out and dried at room temperature for 50 hours to obtain a cell culture film 1 comprising the coating layer on the surface of the hydrophilic PES membrane. Incidentally, a value obtained by dividing a difference between masses of the membrane before and after coating by the surface area was calculated as mass per unit area of the polymer in the coating layer and then found to be 400 μg/$cm^2$.

Examples 2 to 4 and Comparative Example 1

A coating layer was formed on the surface of the hydrophilic PES membrane in the similar manner to Example 1, except that, in Example 1, the concentrations of the polymer solutions were set to 0.1% by mass, 0.05% by mass, 0.01% by mass, and 0.001% by mass, respectively, thereby obtaining cell culture films 2 to 5. Incidentally, the masses per unit area of the polymers in the coating layer were 60 μg/$cm^2$, 36 μg/$cm^2$, 10 μg/$cm^2$, and 2 μg/$cm^2$, respectively.

Comparative Example 2

The hydrophilic polyether sulfone membrane before being coated with the polymer 1 was used as a cell culture film 6 without any changes.

Results obtained by measuring the contact angle of the surface of the coating layer to water in each cell culture film by the above-described method are presented in the following Table 1.

<Contact Angle Measurement>

The contact angle of a surface of the coating layer to water was measured by a contact angle meter (measurement method; according to JIS R 3257:1999 (sessile drop method)). Results are presented in the following Table 1.

<Cell Adhesion Activity Assay>

As cells, human adipose tissue-derived mesenchymal stem cells (Lonza, Walkersville, Maryland, U.S.A.) were used. The donor was a 22-year-old man and the prepared cells were expressed CD13, CD29, CD44, CD73, CD90, CD105, SD166≥90%, CD14, CD31, CD45≤5%

The human adipose tissue-derived mesenchymal stem cells were seeded on the 96-well tissue culture polystyrene dishes on which the cell culture films 1 to 6 are disposed to be 8×10³ cells/well, and then cultured for one day in Mesenchymal Stem Cell Growth Medium 2 (PromoCell GmbH, Bedford, Massachusetts, U.S.A.) under humidified condition at 37° C. in the presence of 5% $CO_2$. After the completion of culture, the culture medium was exchanged with Mesenchymal Stem Cell Growth Medium 2 containing 10% WST-1 (Premix WST-1 Cell Proliferation Assay System, Takara Bio Inc., Shiga, Japan) and then cultured for 4 hours under humidified condition at 37° C. in the presence of 5% $CO_2$, and then the absorbance (450 nm, comparison 600 nm) of culture supernatant was measured by a microplate reader and regarded as cell adhesion activity. Results are presented in the following Table 1.

<Cell Proliferation Activity Assay>

The same human adipose tissue-derived mesenchymal stem cells as those used in the cell adhesion activity assay were seeded on the 96-well tissue culture polystyrene dishes on which the cell culture films 1 to 6 are disposed to be 4×10³ cells/well, and then cultured for three days in Mesenchymal Stem Cell Growth Medium 2 (PromoCell GmbH, Bedford, Massachusetts, U.S.A.) under humidified condition at 37° C. in the presence of 5% $CO_2$. After the completion of culture, the culture medium was exchanged with Mesenchymal Stem Cell Growth Medium 2 containing 10% WST-1 (Premix WST-1 Cell Proliferation Assay System, Takara Bio Inc., Shiga, Japan) and then cultured for 4 hours under humidified condition at 37° C. in the presence of 5% $CO_2$, and then the absorbance (450 nm, comparison 600 nm) of culture supernatant was measured by a microplate reader and regarded as cell proliferation activity. Results are presented in the following Table 1.

TABLE 1

| | Cell culture film | Coating | Concentration % by mass) of polymer solution | Coating amount (μg/cm²) | Contact angle (°) | Cell adhesion activity | Cell proliferation activity |
|---|---|---|---|---|---|---|---|
| Example 1 | 1 | Polymer 1 | 1.0 | 400 | 69 | 0.135 | 0.145 |
| Example 2 | 2 | Polymer 1 | 0.1 | 60 | 52 | 0.087 | 0.114 |
| Example 3 | 3 | Polymer 1 | 0.05 | 36 | 50 | 0.083 | 0.112 |
| Example 4 | 4 | Polymer 1 | 0.01 | 10 | 30 | 0.076 | 0.110 |
| Comparative Example 1 | 5 | Polymer 1 | 0.001 | 2 | 20 | 0.072 | 0.083 |
| Comparative Example 2 | 6 | None | — | 0 | 20 | 0.080 | 0.080 |

As presented in the above Table 1, the cell culture films 1 to 4 which have a coating amount of the polymer of more than 2 μg/cm² exhibited excellent cell proliferation activity as compared to the cell culture films 5 and 6 which have a coating amount of the polymer of 2 μg/cm² or less or which are not coated. Incidentally, the cell culture film 4 did not show a large difference in cell adhesion activity as compared to the cell culture film 6 which is not coated with the polymer, but exhibited significantly improved cell proliferation activity. The reason for this is not clear but is presumed that the integrin binding site of the cell-adhesive protein adsorbed to the surface faces the side of the cells to exhibit favorable cell proliferation activity.

The invention claimed is:

1. A cell culture substrate comprising a coating layer on at least one surface of a hydrophilic polymer substrate, wherein the coating layer includes a polymer consisting of structural units of a single furfuryl acrylate monomer represented by the following Formula (1), and a ratio of mass of the polymer contained per unit area of the coating layer is more than 2 μg/cm²:

[Chem. 1]

Formula (1)

wherein, $R^1$ represents a hydrogen atom or a methyl group, and $R^2$ represents a group represented by the following Formula (1-1) or the following Formula (1-2):

[Chem. 2]

Formula (1-1)

Formula (1-2)

wherein, $R^3$ represents an alkylene group having 1 to 3 carbon atoms.

2. The cell culture substrate according to claim 1, wherein the hydrophilic polymer substrate contains at least one selected from the group consisting of polyamide, polyethersulfone, polyarylethersulfone, and polyvinylpyrrolidone.

3. A bioreactor comprising the cell culture substrate according to claim 1.

4. A method for culturing stem cells using a bioreactor according to claim 3, comprising:
   seeding the stem cells on the cell culture substrate in the bioreactor.

5. A bioreactor comprising the cell culture substrate according to claim 2.

6. A method for culturing stem cells using a bioreactor according to claim 5, comprising:
   seeding the stem cells on the cell culture substrate in the bioreactor.

7. The cell culture substrate according to claim 1, wherein the single furfuryl acrylate monomer is selected from the group consisting of tetrahydrofurfuryl acrylate, tetrahydrofurfuryl methacrylate, furfuryl acrylate, furfuryl methacrylate, 5-[2-(acryloyloxy)ethyl]tetrahydrofuran, 5-[2-(methacryloyloxy)ethyl]tetrahydrofuran, 5-[2-(acryloyloxy)ethyl]furane, and 5-[2-(methacryloyloxy)ethyl]furane.

* * * * *